(12) United States Patent
Fan (10) Patent No.: US 10,433,835 B1
(45) Date of Patent: Oct. 8, 2019

(54) PUSH-TWIST SUTURE-PASSING LAPAROSCOPIC KNOT TYING INSTRUMENT

(71) Applicant: Peter Fan, Englewood Cliffs, NJ (US)

(72) Inventor: Peter Fan, Englewood Cliffs, NJ (US)

(*) Notice: Subject to any disclaimer, the term of this patent is extended or adjusted under 35 U.S.C. 154(b) by 0 days.

(21) Appl. No.: 16/197,572

(22) Filed: Dec. 20, 2018

Related U.S. Application Data

(63) Continuation-in-part of application No. 16/010,601, filed on Nov. 21, 2018.

(51) Int. Cl.
*A61B 17/04* (2006.01)

(52) U.S. Cl.
CPC ...... *A61B 17/0469* (2013.01); *A61B 17/0491* (2013.01); *A61B 2017/0474* (2013.01)

(58) Field of Classification Search
CPC ............ A61B 2017/2906; A61B 17/28; A61B 17/2812; A61B 17/2841; A61B 17/29; A61B 2017/2901; A61B 2017/2902; A61B 2017/2903; A61B 17/2909; A61B 2017/2912; A61B 2017/2913; A61B 2017/2915; A61B 2017/2916; A61B 17/0469
See application file for complete search history.

(56) References Cited

U.S. PATENT DOCUMENTS

| | | | | |
|---|---|---|---|---|
| 5,336,230 A | * | 8/1994 | Leichtling | A61B 17/0469 128/898 |
| 5,759,188 A | * | 6/1998 | Yoon | A61B 17/0469 606/147 |
| 7,998,149 B2 | * | 8/2011 | Hamilton | A61B 17/062 606/144 |
| 2012/0239080 A1 | * | 9/2012 | Fan | A61B 17/0469 606/205 |
| 2018/0125480 A1 | * | 5/2018 | Fan | A61B 17/0483 |

* cited by examiner

*Primary Examiner* — Thomas M McEvoy (57) ABSTRACT

This is a laparoscopic instrument for facilitating intracorporeal tying of knots. The shafts of two small diameter laparoscopic graspers are combined within a common external sheath. One grasper has a regular scissors handle, is stationary, and acts as a recipient grasper, while the other has no handle, but is rotatable and slidable, and acts as a donor grasper. It enables the head end of a suture to be actively passed from the jaws of the donor grasper to the jaws of the adjacent recipient grasper, after passing behind and around the tail strand, thus forming a knot. The current version of this instrument introduces two additional features, one being the passive production of the rotation by the straight sliding mechanism, the other being the use of free-wheeling levers allowing rotation of the shaft of the donor grasper, without rotating the attached levers in the slots.

2 Claims, 13 Drawing Sheets

4 was deleted

PUSH-TWIST SUTURE-PASSING LAPAROSCOPIC KNOT TYING INSTRUMENT

FIELD OF INVENTION

The tying of knots in a suture intra-corporeally with laparoscopic instruments is difficult and time consuming. Surgeons are still in need of an instrument that would facilitate this tying process. The present device combines two graspers in one instrument to be used in one hand and enables the passing of the head end of a suture from a donor grasper to an adjacent recipient grasper behind the tail end of the same suture, thereby creating the knot.

BACKGROUND OF THE INVENTION

Tying of knots is essential in any kind of surgery. It is relatively easy in open surgery but is difficult in laparoscopic surgery. The current art of laparoscopic knot tying employs either the extra-corporeal method, involving tying the knot by hand outside the body and pushing the knot inside with a knot pusher, or the intra-corporeal method, involving manipulation of the suture with the tips of two laparoscopic graspers, which is slow and cumbersome, and requires considerable skill. Laparoscopic clip appliers, staplers, pre-tied knots and the like are useful substitutes, but cannot totally replace tied knots which are still needed. Despite considerable prior art, today hardly any hand operated instrument exists that renders laparoscopic intra-corporeal knot tying easier and faster.

Figure 1:
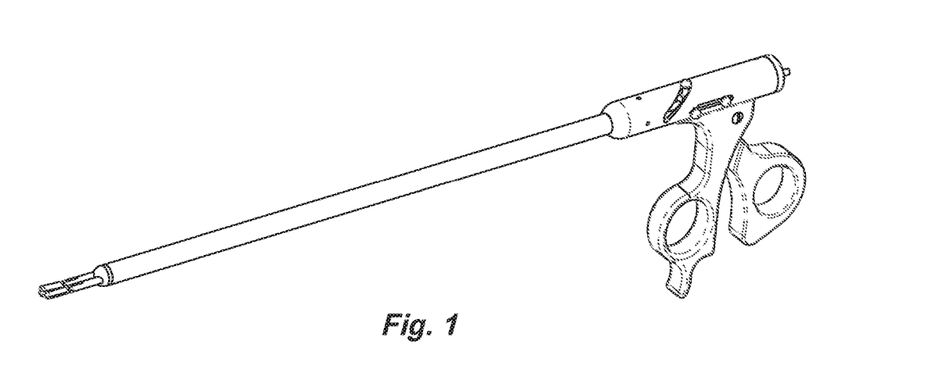
FIG. 1 is a perspective view of the entire instrument from the left side.
Figure 2:
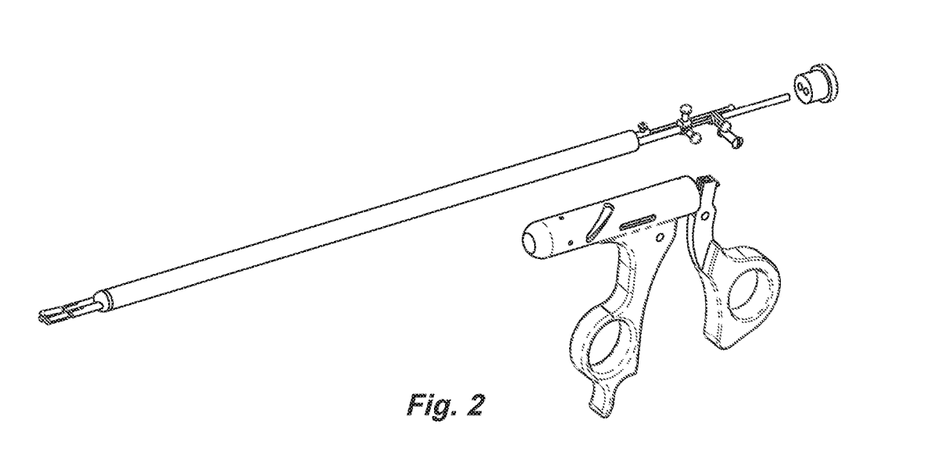
FIG. 2 is an exploded view of the handle end of the instrument.
Figure 3:
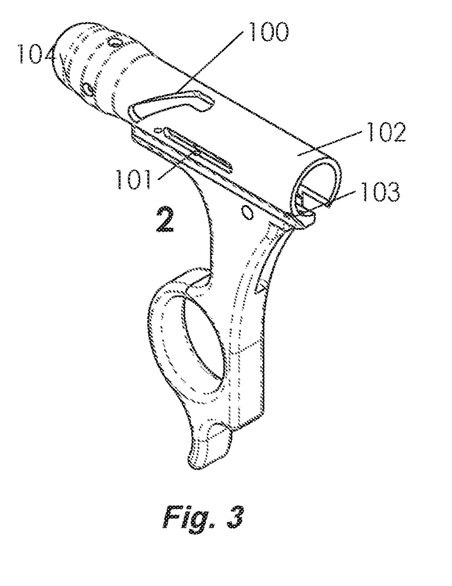
Figure 4:
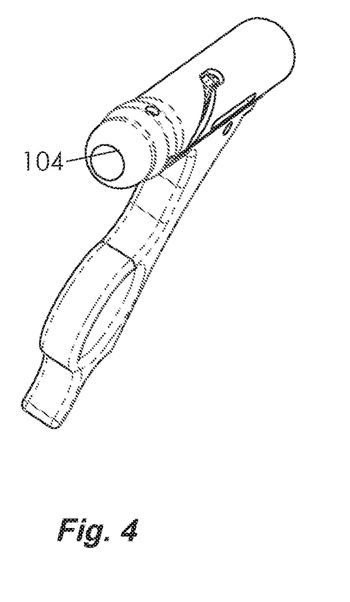
FIG. 4 is another perspective view of the stationary handle. 104 is a large opening at the front end of the chamber, for exit of the front end of the main sheath sub-assembly.
Figure 5:
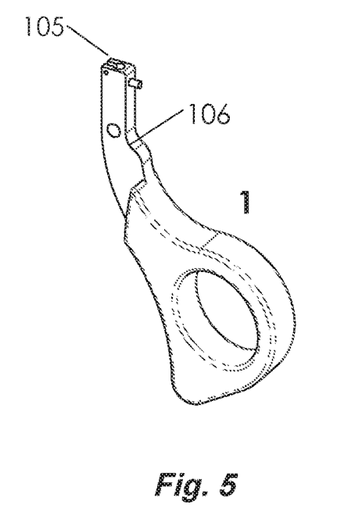
FIG. 5 is a perspective view of the movable handle. 105 is a receptacle for the ball to form the ball-joint. 106 is a narrow upper stem of the movable handle, with a cut out.
Figure 6:
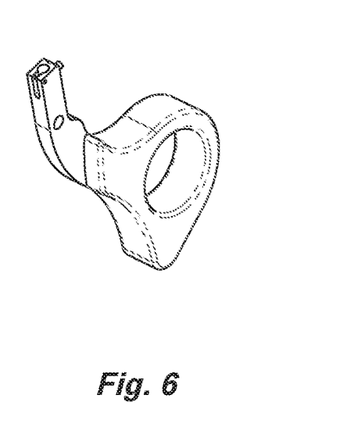
FIG. 6 is another perspective view of the movable handle.
Figure 7:
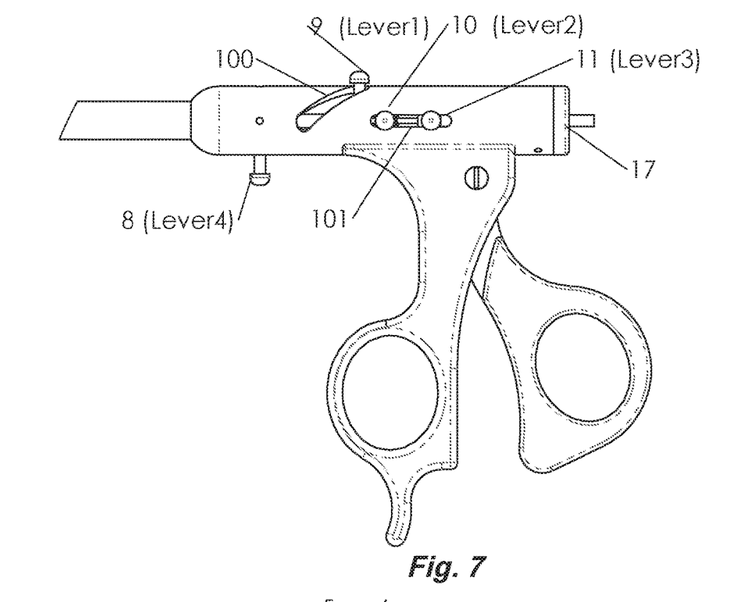
Figure 8:
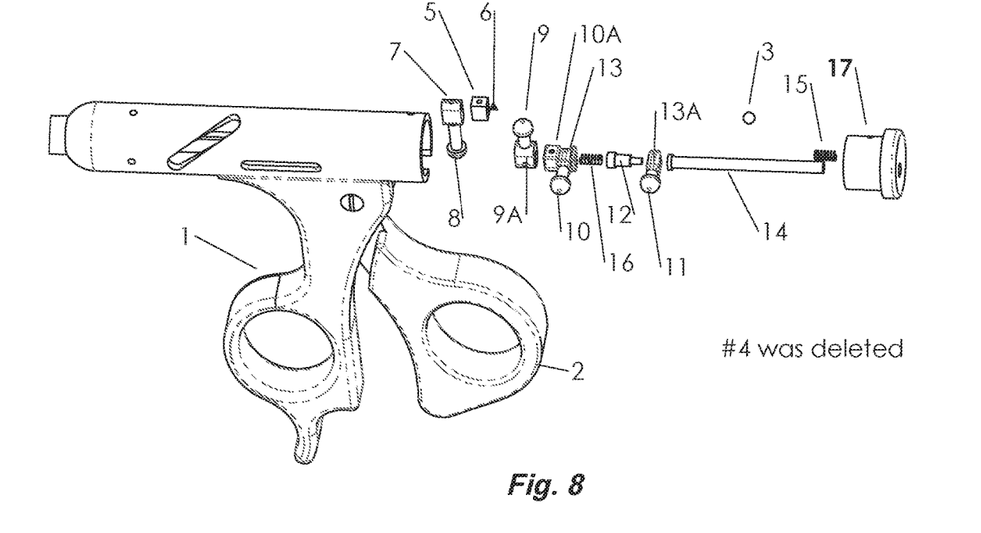
Figure 9:
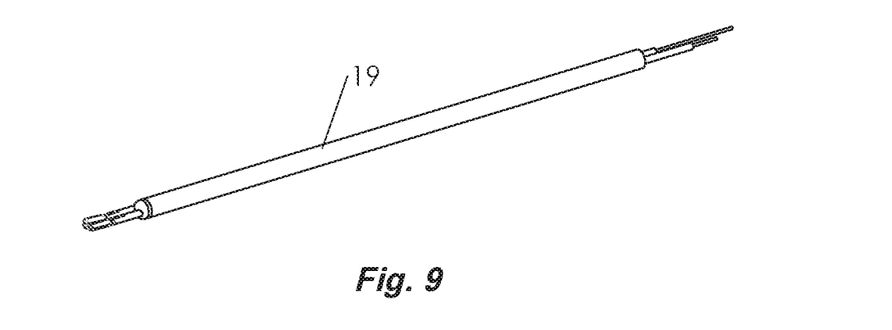
FIG. 9—shows the main sheath sub-assembly, minus the two handles. 19 is the main sheath.
Figure 10:
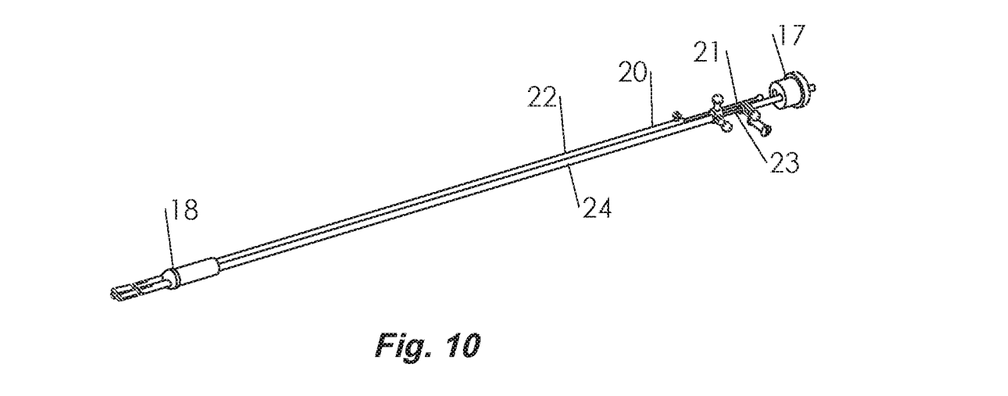
FIG. 10—shows a view of the main sheath sub-assembly, minus the main sheath, showing its numerous components. 18 is the front spacer. 19 is the main sheath. 20 is the rear spacer (different from the rear plug). 21 is the right rod whose right end is attached to a ball. 22 is the right grasper sheath. 23 is the left rod, whose right end is attached to the Mini-Adaptor and the Rod-Extension. 24 is the left grasper sheath.
Figure 11:
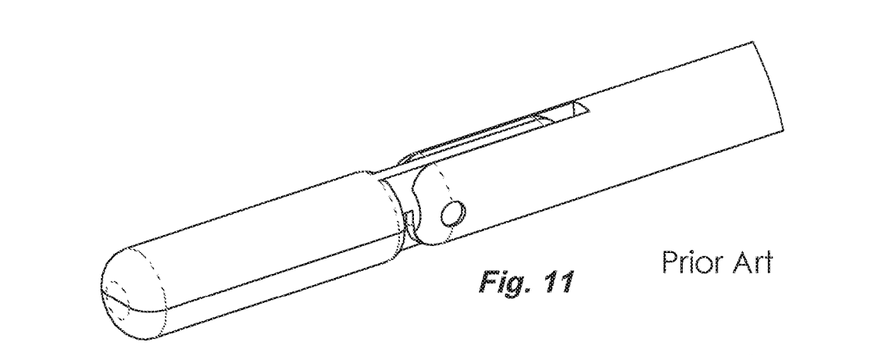
FIG. 11—shows both jaws closed. These jaws are Prior Art.
Figure 12:
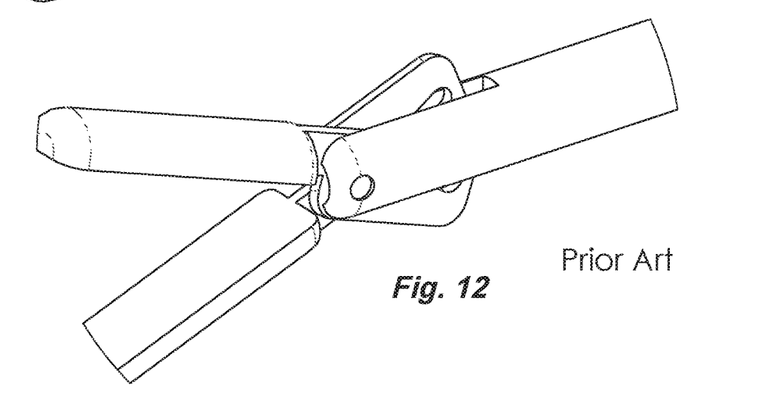
FIG. 12—shows both jaws fully opened to 45 degrees.
Figure 13:
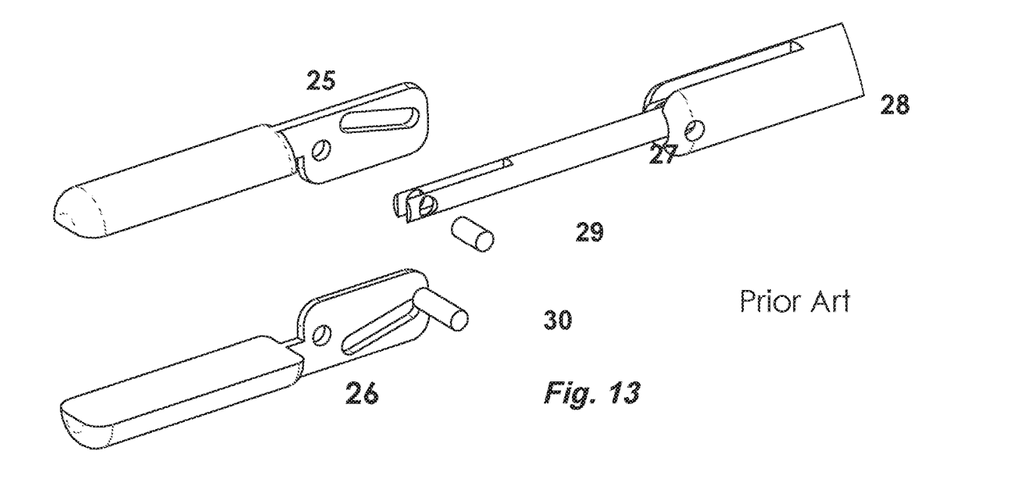
Figure 14:
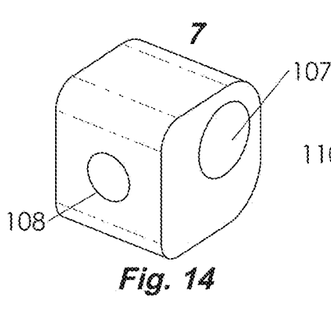
FIG. 14 shows part #7, the Adaptor-4, with 107 for the right rod, and 108 for the Lever 4.
Figure 15:
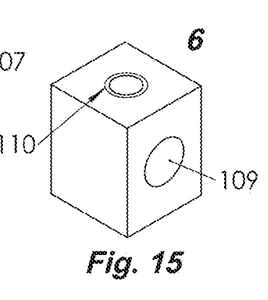
FIG. 15 shows part #6, the Adaptor-5, with 109 for the right rod, and 110 for the mini-screw. This is used for trapping the compression spring, and does not have a lever.
Figure 16A:
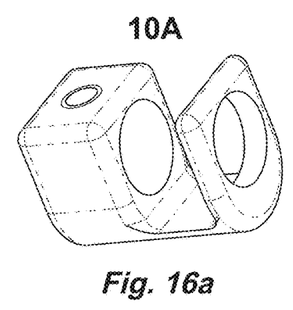
FIG. 16a shows part #10 A, the U-shaped Adaptor, which houses the Free-wheeling Adaptor part #13.
Figure 16B:
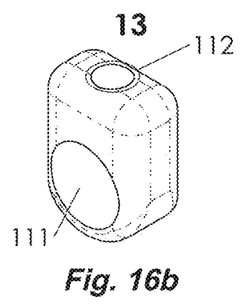
FIG. 16b shows the free-wheeling adaptor, part #13, with 111 for the sheath of the donor grasper, and 112 for the Lever-1.
Figure 17:
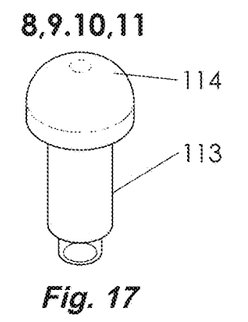
FIG. 17 shows the Universal Lever, which is the same for the parts of, 8, 9, 10, and 11. 113 is the Lever itself, and 114 is the head of the lever.
Figure 18:
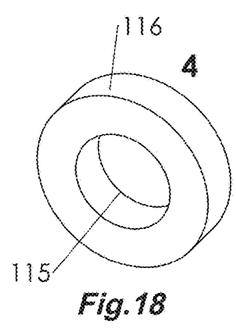
FIG. 18 is a Washer, part #16, for retaining the spring, and preventing the spring from contacting the ball. 115 allows passage of the right rod. 116 is the rim.
Figure 19:
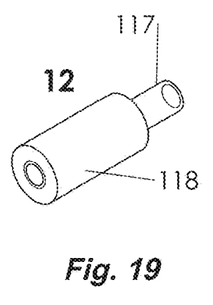
FIG. 19 is the small Mini-Adaptor-3, part #12, whose male thread 117 screws through hole 111 of part 13A, into the female thread 119 of the Rod-Extension, part #14. 118 is a flange.
Figures 19B, 20:
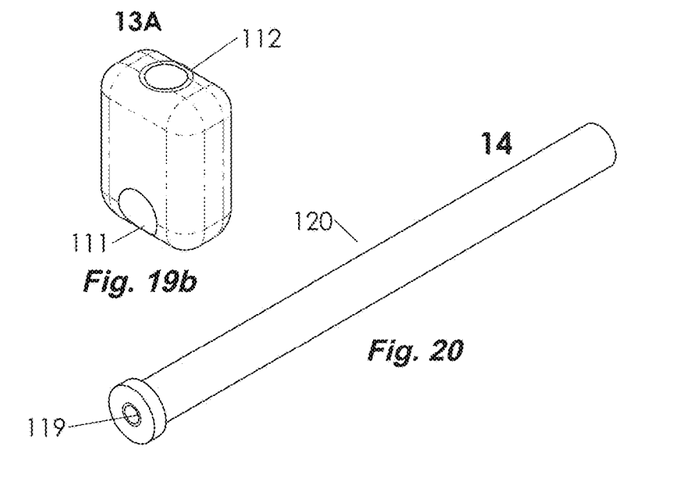
FIG. 19b is a second Free-wheeling Adaptor, part 13A. 111 is for passage of the rod. 112 is for attaching the Lever-3.
FIG. 20 is the long Rod-Extension, part #14. 120 is a flange for retaining the free wheel Adaptor #13A.
Figure 21:
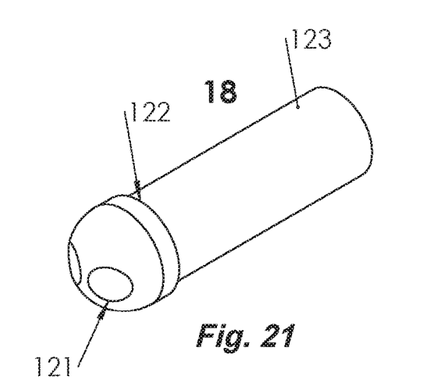
FIG. 21 shows the Front Spacer. Part #18. 121 is a tunnel for the sheath of the left grasper. 122 is a flange. 123 is the shaft.
Figure 22:
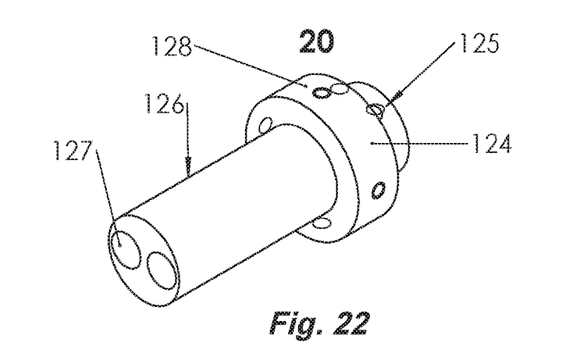
Figure 23:
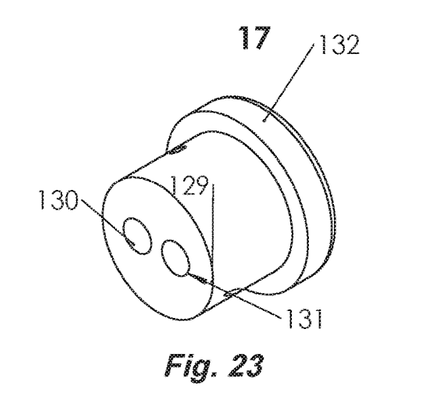
Figure 24:
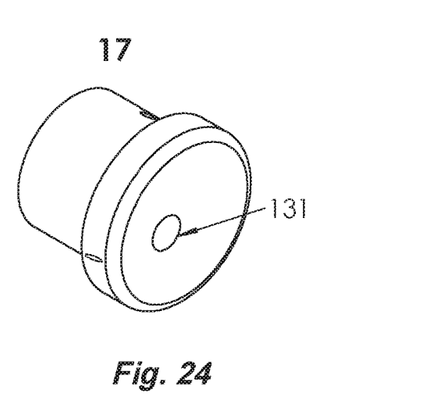
Figure 25:
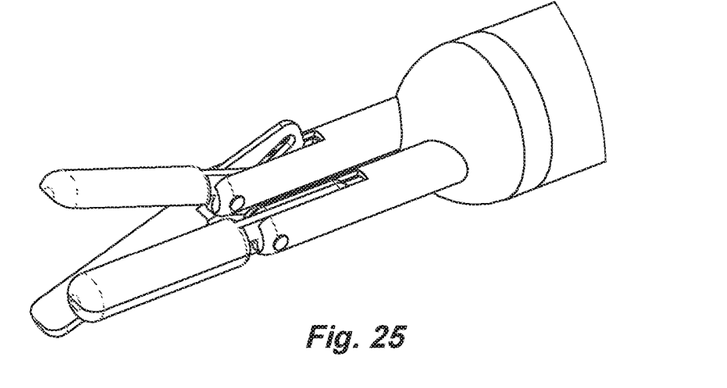
FIG. 25 shows the resting positions of the jaws of the instrument, one open, one closed.
Figure 26:
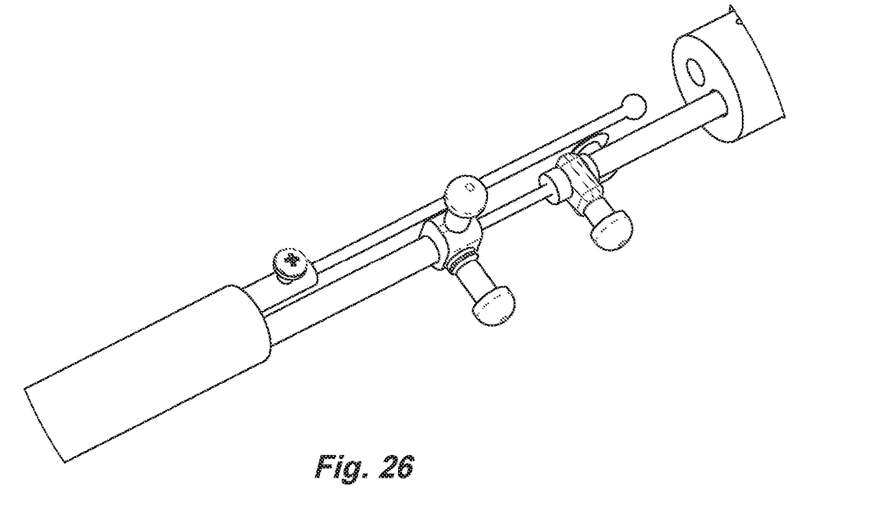
FIG. 26 shows the detailed assembled mechanisms inside the tubular chamber at the top of the instrument.
Figure 27:
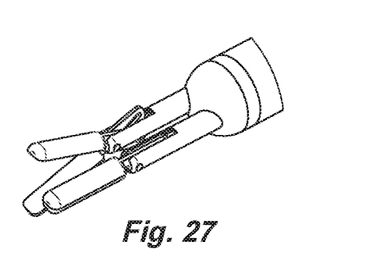
FIG. 27 shows the jaw positions at rest.
Figure 28:
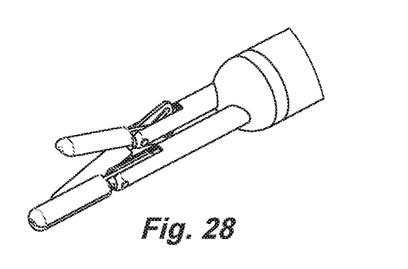
FIG. 28 shows the donor grasper extended.
Figure 29:
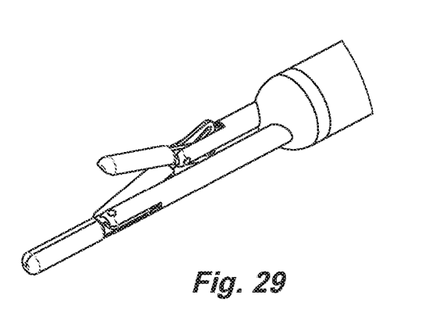
FIG. 29 shows the jaws rotating from horizontal to vertical position.
Figure 30:
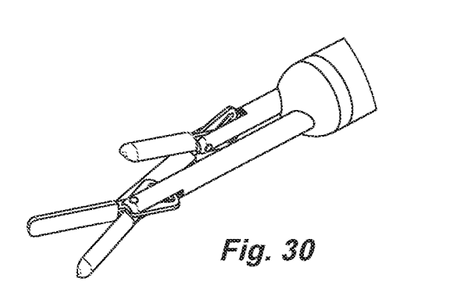
FIG. 30 shows the vertical jaws opening.
Figure 31:
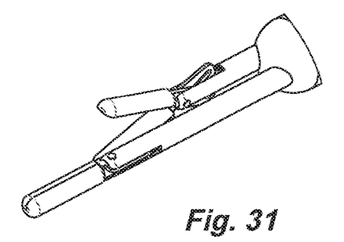
FIG. 31 shows the vertical jaws closing.
Figure 32:
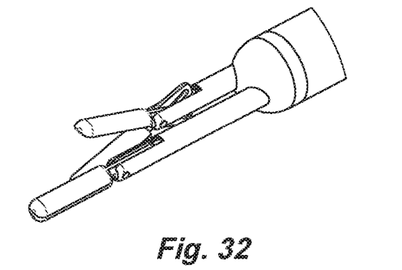
FIG. 32 shows the vertical jaws de-rotating back to horizontal.
Figure 33:
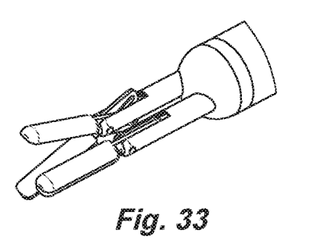
FIG. 33 shows the horizontal jaws returning to original starting position.
Figure 34:
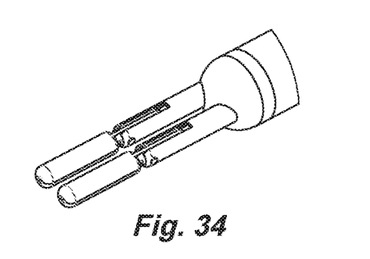
FIG. 34 shows the jaws of the recipient grasper closing and taking over.
Figure 35:
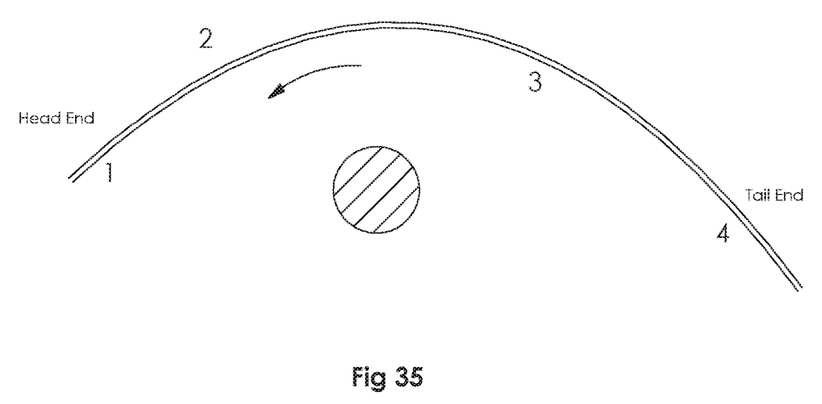
FIG. 35 shows the Naming of the different parts of a suture in the tying process. 1 is the Head End, 2 is the Head Strand, 3 is the Tail Strand, 4 is the Tail End.
Figure 36:
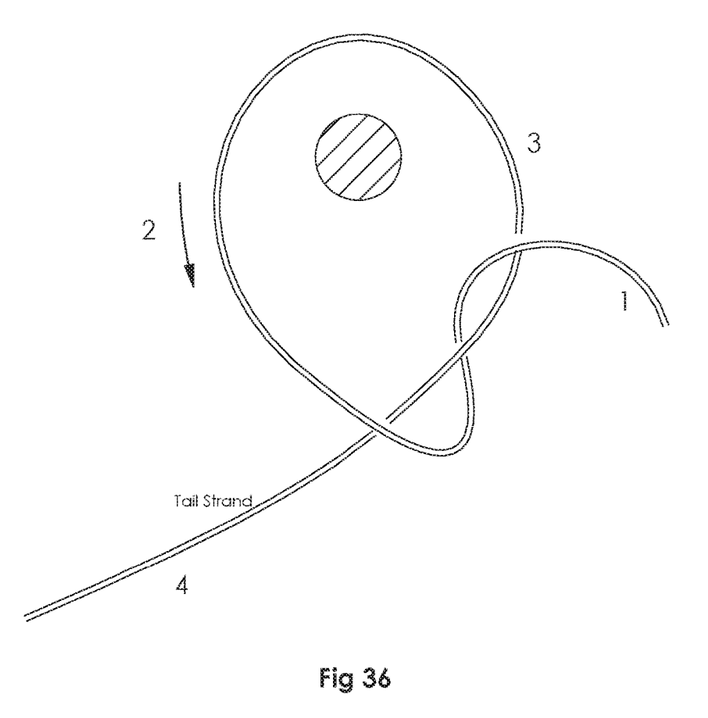
FIG. 36 shows the Head End traveling over, under, and over again the Tail Strand Sheet 11—
Figure 37:
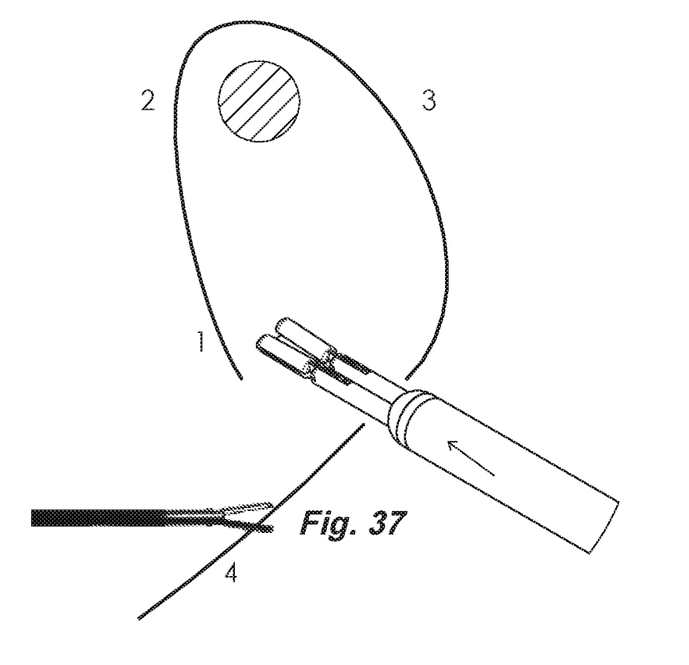
FIG. 37—shows the entire instrument advancing forwards over the tail strand, and grasping the head end of the suture with the jaws of the donor grasper.
Figure 38:
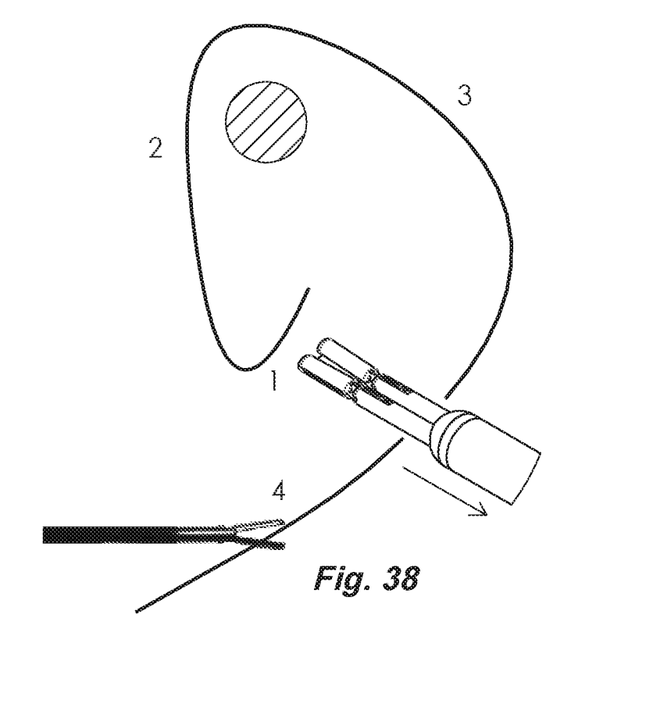
FIG. 38—shows pulling back the entire instrument over the tail strand.
Figure 39:
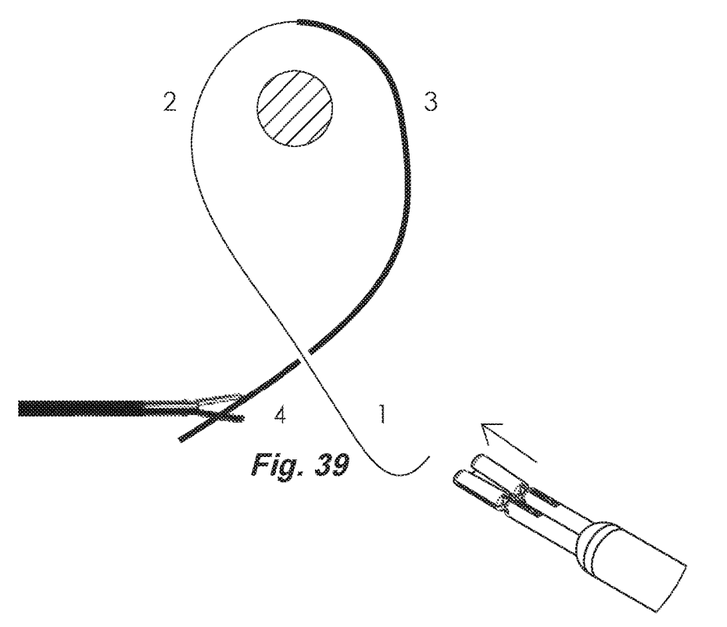
FIG. 39—shows pushing forwards the entire instrument, carrying the head end of the suture with it, and trapping the tail strand in the gap between the tips of the two graspers, with the donor grasper on the underside.
Figure 40:
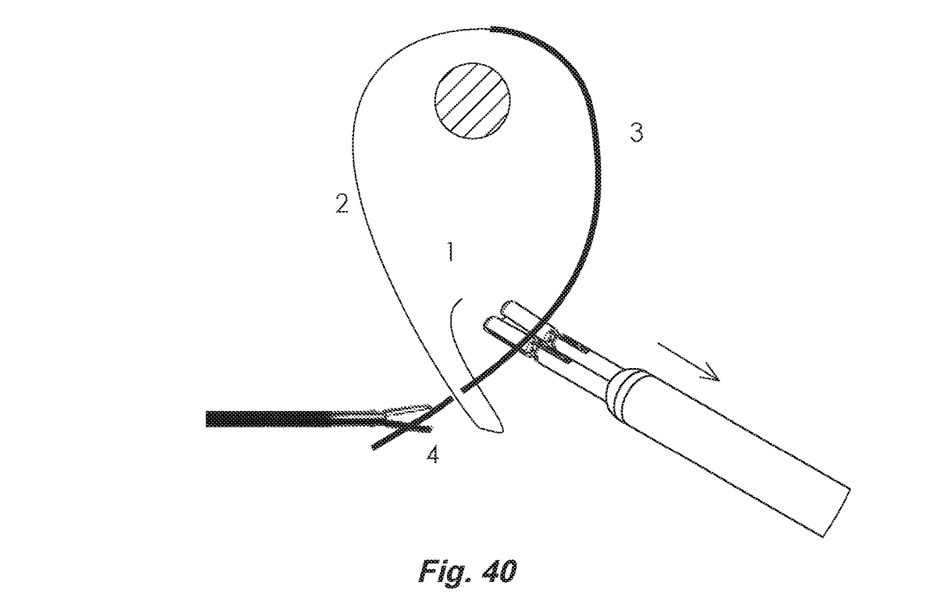
FIG. 40—shows the return of the jaws of the donor grasper to the original position, prior to closing jaws of the recipient grasper.
Figure 41:
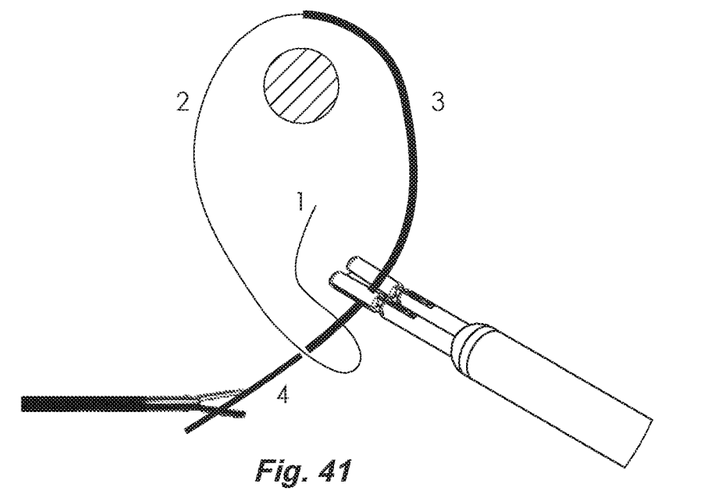
FIG. 41—shows the jaws of the recipient grasper about to close on the head end of the suture.
Figure 42:
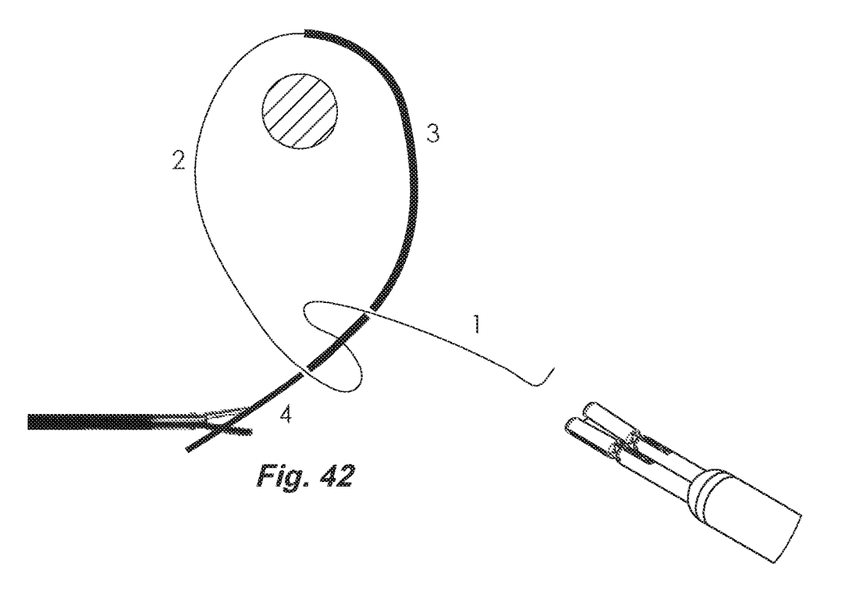
FIG. 42—shows the recipient grasper taking over the head end of the suture and pulling away to form the knot.

In order to describe the tying process, the different parts of a suture ligature need first be given names. As shown in FIG. 18 in the drawings, after the suture ligature has passed around the tissue to be tied, it then presents with a head end (1), a head strand (2), a tail strand (3), and a tail end (4).

There are three basic methods of tying a knot, whether done openly or laparoscopically. The first method makes the head end of the suture pass 360 degrees continuously around the tail strand, as is shown in the U.S. Pat. No. 9,561,028, "Automatic Laparoscopic Knot Tier", invented by this author, and was designed specifically to avoid the release and re-grab.

The second method makes a loop, which is commonly used by surgeons performing open surgery, where the surgeon makes "instrument ties", by wrapping the tail strand of the suture around the needle holder, and then pulling the head end of the suture through the loop. The instrument described in the U.S. Pat. No. 9,820,736, invented also by this author, makes such a loop laparoscopically.

The third method involves making a "throw", which actively passes the head end of the suture behind its tail strand, between two adjacent graspers. This simulates the tying of shoe-laces by fingers and requires the release and re-grab of the head end of the suture, behind the tail strand, which is now the object of the present invention.

In the present invention, two small diameter laparoscopic graspers are incorporated inside a common external sheath, with one being stationary and keeping a regular scissors type of handle, known as the recipient grasper, and the other losing its handle, becoming rotatable, as well as slide-able, known as the donor grasper.

Referring to the author's own previous attempts, the first was the "Double Laparoscopic Grasper", U.S. Ser. No. 13/051,992, which was abandoned because the passing of the suture between the two graspers could not be accomplished at that time. The author's second attempt was the "Automatic Laparoscopic Knot Tying Instrument", U.S. Pat. No. 9,561,028, which uses a mini-grasper at the tip of the instrument grasping the head end of the suture, then rotating through 360 degrees around the tail strand, and avoiding the release and re-grab of the head end of the suture. The author's third attempt was the "Laparoscopic Suture Loop Maker", U.S. Pat. No. 9,820,736, which worked quite well, but also avoided the release and re-grab. However, the $2^{nd}$ and $3^{rd}$ inventions were not fully practicable because, after the knot was made, the final take away depended on springs holding on to the head end of the suture, which proved inadequate. The holding power of the jaws was improved in the $4^{th}$ invention, by incorporating a scissors type of handle and using the power of the thumb, U.S. patent application Ser. No. 15/859,717, which also included the element of rotation, which although worked, was not ideal, because it depended on the use of the unreliable 90-degree jaws. A subsequent Continuation-in-Part added sliding to avoid the use of the 90-degree jaws. The current instrument further improves by automatically producing the rotation during the sliding, and further enables the use of the standard double-acting 45-degree laparoscopic grasper jaws.

Referring to the previous literature, the Christoudias Double Grasper has 3 jaws, with a common middle jaw, but functions as a tissue approximator. Its spring-loaded actuators are operated by two push buttons. The Ferzli Double Grasper, has a second pair of jaws positioned more proximally on the main shaft, whose purpose is to anchor one end of the suture prior to twisting it around the shaft of the instrument in order to produce a loop. The Hasson Suture Tying Forceps, is similar to the Ferzli, with 3 finger loops. The orthopedic suture passers are for passing sutures only through hard tissue, and these include the Arthrex Scorpion Suture Passer, and the Arthrex Birdbeak Suture Passer. Some suture passers are for passing sutures through a thickness of soft tissue such as the abdominal wall, and these include the Goretex and the Aesculap. There are devices which "pass the suture-needle" side to side, for inserting sutures into tissues, as well as for tying knots, e.g. the Autosuture's Endo-stitch, and the Japanese Maniceps. Note these only pass the suture needle, not the suture thread per se. There have been devices that attempt to "automatically" tie a knot, such as Jerrigan's experimental rotating slotted disc designed for robotic endo-cardiac surgery, but it was abandoned because of the requirement for a manufactured cartridge.

There have been also many devices that help to "create a loop", but with each functioning differently—(a) Kitano's grasper with the rotating sleeve, Japanese, (b) Donald Murphy's grasper with the extra hom, Australian, (c) Grice's sleeve catching instrument, (d) Bagnato & Wilson's device which simulates the radiological pig-tail catheter, with a preformed loop built into the tip of the catheter, which is deformable and purportedly a loop former, but it is difficult to manufacture and apply, and has not yet been reduced to practice, (e) Ferzli's double grasper, which anchors one end of the suture, as described above. There have been devices using a "pre-formed knot", (1) Ethicon's Endo-Loop, (2) the Duraknot, (3) LSI's device, (4) Pare's pre-tied knot, all of which do not help to tie knots.

Other past inventions related to intra-corporeal laparoscopic knot tying fail to address the basic problem of "how to create a knot". They usually offer various alternatives, such as making fishing knots, using pre-tied knots, knot pushers, suture clips, cinchers, tissue fasteners, anchors, stapling devices, etc. The present invention however actively passes the head end of the suture behind its tail end, from one grasper to another grasper, to make the actual knot intra-corporeally.

| U.S. patent documents | | | | |
|---|---|---|---|---|
| 1. | 3,834,395 | Sep. 10, 1974 | Manuel Santos | 128/326 |
| 2. | 5,201,759 | Apr. 13, 1993 | George Ferzli. | 606/139 |
| 3. | 5,217,471 | Jun. 8, 1993 | Stephen Burkhart | 606/148 |
| 4. | 5,234,443 | Aug. 10, 1993 | Phan & Stoller | 606/148 |
| 5. | 5,250,054 | Oct. 5, 1993 | Lehmann Li | 606/148 |
| 6. | 5,281,236 | Jan. 25, 1994 | Bagnato et al. | 606/139 |
| 7. | 5,312,423 | May 17, 1994 | Rosenbluth & Brenneman | 606/148 |
| 8. | 5,395,382 | Mar. 7, 1995 | DiGiovanni et al. | 606/148 |
| 9. | 5,437,682 | Aug. 1, 1995 | Drew Grice | 606/148 |
| 10. | 5,423,836 | Jun. 13, 1995 | Scott Brown | 606/148 |
| 11. | 5,439,467 | Aug. 8, 1995 | Theodore Benderev, et al. | 606/139 |
| 12. | 5,480,406 | Jan. 2, 1996 | Nolan et al. | 606/139 |
| 13. | 5,728,109 | Mar. 17, 1998 | Schulze et al. | 606/148 |
| 14. | 5,810,852 | Sep. 22, 1998 | Greenberg et al. | 606/148 |
| 15. | 5,814,054 | Sep. 29, 1998 | Kortenbach et al. | 606/139 |
| 16. | 5,846,254 | Dec. 8, 1998 | Schulze et al. | 606/228 |
| 17. | 6,051,006 | Apr. 18, 2000 | Shluzas & Sikora | 606/148 |
| 18. | 6,086,601 | Jul. 1, 2000 | InBae Yoon | 606/148 |
| 19. | 6,221,084 | Apr. 24, 2001 | R. Fleenor, Pare Surgical | 606/148 |
| 20. | 6,432,118 | Aug. 13, 2002 | Mollenhauer & Kucklick | 606/148 |
| 21. | 6,716,224 | Apr. 26, 2004 | Singhatat | 606/148 |
| 22. | 2009/0228025 | Sep. 10, 2009 | Steven Benson | 606/144 |
| 23. | 2010/0016883 | Jan. 21, 2010 | George Christoudias | 606/205 |
| 23. | 5,312,423 | May 17, 1994 | Rosenbluth et al. | 606/148 |
| 25. | 8,512,362 | Aug. 20, 2013 | Ewers et al. | 606/158 |
| 26. | 4,635,638 | January 1987 | Weintraub. | |
| 27. | 5,938,668 | August 1999 | Scirica. | |
| 28. | 5,954,731 | September 1999 | Yoon. | |
| 29. | 6,017,358 | January 2000 | Yoon | |
| 30. | 6,086,601 | July 2000 | Yoon. | |
| 31. | 2008/0228204 | September 2008 | Hamilton. | |
| 32. | 2013/051992 | Sep. 30, 2012 | Fan—Double Laparoscopic Grasper | |
| 33. | 9,561,028 | Feb. 7, 2017 | Fan—Automatic Lap. Knot Instrument | |
| 34. | 9,820,736 | Nov. 1, 2017 | Fan—Laparoscopic Suture Loop Maker. | |
| 35. | 15/859,717 | Jan. 1, 2018 | Fan—Suture Passing Laparoscopic Knot-tier. | |
| 36. | 16/010,601 | Jun. 18, 2018 | Fan—Push-Twist Suture-Passing Laparoscopic Knot Tying Instrument. | |

OTHER PUBLICATIONS

1. Endo-stitch—Autosuture—Manufacturer's item #173016.
2. Maniceps—Japanese suturing device, similar to Endo-stitch.
3. A Laparoscopic Device for Minimally Invasive Cardiac Surg. Shaphan Jemigan, et. al.—European J. of Cardiothoracic Surgery, Vol. 37, p. 626-630. March 2010.
4. Knot Tying Intra-corporeally, with newly designed Forceps. (sliding sleeve).
5. Kitano et. al.—J. of Minimal Invasive Therapy & Allied Tech, 1996. 5: 27-28.
6. Endoscopic Knot Tying Made Easier—(one jaw with extra bump).
7. Donald Murphy—ANZ J. Surg. 1995. 65, 507-509.
8. The Excalibur Suturing Needle Holder—(jaw with prominent heel, helps looping)
9. Uchida et. al. Surgical Endoscopy—vol. 3, 531-532
10. Alijizawi laparoscopic auto-knot device—(two dissolving balls).
11. A New Reusable Instrument designed for simple and secure knot tying in laparoscopic surgery. S. S. Miller 1996 Surg. Endos 10: 940-941 (pointed canula).
12. The Nobel Automatic Laparoscopic Knotting and Suturing Device. Mishra et. al. World Laparoscopy Hospital, India. (a knot pusher)
13. Automated Knot Tying for Fixation in Minimally Invasive Robot Assisted Cardiac Surgery. March 9(1):105-12.
14. Kuniholm & Buckner—J. Biomed Engino 2005, Vol. 127, 1001-8. JSLS. 2005 January
15. M I Frecke—Laparoscopic multifunctional instruments: design and testing. Endosc Surg Allied Technol. 1994 December; 2(6):318-9.
16. G. Berci—Multifunctional laparoscopic Instruments.
17. http://www.ligasure.com/ligasure/pages.aspx?page=Products/Laparoscopic
18. http://www.freepatentsonline.com/y2010/0063437.
19. http//www.ncbi.nlm.nih.gov/pubmed/15791983 Multifunctional Laparoscopic Instruments.

SUGGESTED U.S. CLASSIFICATION: 606/139, 144, 145, 148.

SUGGESTED INTERNATIONAL CLASSIFICATION: A61B 17/00, 04, 28.

FIELD OF SEARCH: 606/139, 144, 145, 147, 148, 150, 151, 127, 128, 606/167, 168, 170, 174, 182, 185, 205, 207, 210, 211.

RELATED PRIOR PATENTS: 2013/051,992 U.S. Pat. Nos. 9,194,468, 9,561,028, 9,820,736, Ser. No. 16/010,601.

SUMMARY OF THE INVENTION

In laparoscopic surgery, the tying of knots intra-corporeally is typically performed manually using the tips of two graspers. It is still technically difficult and requires considerable skill and practice. The advent of laparoscopic clips and staples has been a great blessing to surgeons, but cannot totally replace the use of tied knots, which is still necessary. The instrument presented here not only enables the passing of the head end of suture between two adjacent graspers, behind and around the tail end of the suture, but allows the use of the simple double-acting 45-degree laparoscopic jaws, and in addition, introduces a mechanism that automatically creates the necessary simultaneous rotation during the sliding of the handle-less grasper, simplifying the maneuvers. It conforms to the customary shape and size of a laparoscopic instrument, with an elongated round sheath, a regular scissors type of handle at the proximal end, and two small diameter grasper tips protruding at the distal end. The jaws of the graspers are controlled manually and by compression springs. The main grasper, known as the recipient grasper, is stationary and non-mobile, and behaves like a regular grasper, with the advantage of using the thumb pressure during the final take-away, while the secondary grasper, known as the donor grasper is without a handle, and is rotatable and slide-able. This combination of the two mini-graspers, one with a handle and one without, enables the passing of the suture from one grasper to another, and is the heart of this device. All the manipulations are performed by the thumb at the handle, namely: opening the jaws of the donor grasper, rotating and sliding the entire donor grasper, and closing the upper jaw of the recipient grasper.

| PART NUMBERS AND NAMES | |
|---|---|
| 1. | Stationary Handle. |
| 2. | Movable Handle. |
| 3. | Ball. |
| 4. | Retaining Washer |
| 5. | Universal Mini-Screw |
| 6. | Adaptor-5. |
| 7. | Adaptor-4. |
| 8. | Lever-4. |
| 9. | Lever-1. 9A = Adaptor-1 |
| 10. | Lever-2. 10A = Adaptor-2 |
| 11. | Lever-3 |
| 12. | Mini-Adaptor-3. |
| 13 + 13A. | Free-Wheel Adaptors |
| 14. | Rod Extension. |
| 15. | Compression Spring-1. |
| 16. | Compression Spring-2. |
| 17. | Rear Plug |
| 18. | Upper Jaw Blade. |
| 19. | Lower Jaw Blade. |
| 20. | Rod |
| 21. | Sheath |
| 22. | Pins |

DETAILED DESCRIPTIONS OF THE DRAWINGS

Sheet 1—

Sheet 2—

FIG. 3 is a perspective view of the stationary handle. The feature 100 is an angled slot on the left side of the tubular chamber on the top of the stationary handle, for the rotating lever 9. 101 is a horizontal slot, for the sliding levers 10 and 11. 102 is the entrance to the rear of the chamber used for the initial entry of the main sheath sub-assembly. 103 is an open vertical slot on the backside of the stationary handle for hiding the upper limb of the movable handle.

Sheet 3—

FIG. 7 is a left side view of the two handles. Feature 100 is the angled slot for producing rotation of the donor grasper. 9 is the rotating lever. 101 is a long horizontal slot for the free-wheeling sliding lever 10, which produces forward and backward sliding of the entire donor grasper, as well as rotation of the grasper, the latter being automatically generated by the lever in the angled slot. 11 is also a sliding lever located at rear portion of the long slot, which opens the spring-controlled jaws of the donor grasper 17 is the rear plug.

FIG. 8 is an exploded view of the handle sub-assembly, showing its main components. 3 is a ball. 4 is a washer used for retaining one end of the spring. 5 is a mini-screw for attaching to 6, the Adaptor-5 to the right rod. 7 is the Adaptor-4 for attaching 8 the Lever-4 for the index finger. 9 is the rotation Lever-1 inside the angled slot. 10 is the Lever-2 that attaches to the U-shaped Adaptor, which in turn is attached to the left grasper sheath. 13A is a free-wheeling adaptor that allows rotation despite the presence of the Lever. 10 is the lever that controls the horizontal motion of the entire donor grasper. 11 is Lever-3 which is connected to a second free-wheel Adaptor 13B, through 12, the Mini-Adaptor-3, which in turn is connected to the Rod Extension for opening the jaws of the donor grasper. 14 is a rod extension with the flange, for connecting to a Mini-Adaptor 12, which is connected to the end of the left rod. 15 and 16 are compression springs. 17 is the Rear Plug, which has a through hole for the Rod-extension, 13, and a slot for hiding the ball joint.

Sheet 4—

Sheet 5—

FIG. 13—shows the components of the 45-degree jaw exploded. 25 is the upper jaw. 26 is the lower jaw, which is identical to the upper jaw. 27 is the rod whose tip is modified to accept the jaws. 28 is the sheath whose tip is similarly modified to accept the jaws.

Sheet 6—

Sheet 7—

FIG. 22 shows the Rear Spacer, Part #20. 124 is the flange. 125 is a threaded hole for locking the sheath of the grasper. 126 is the shaft. 127 are tunnels that align with those on the Front Spacer. 128 are 3 holes for screws fixing the main sheath sub-assembly to the Stationary Handle.

FIGS. 23 & 24 show perspective views of the Rear Plug, part #17, which is the last part to be inserted. 129 is the body. 130 is the open slot to accommodate the upper end of the movable grasper and the ball joint. 131 is the through hole for sliding the rod-extension back and forth. 132 is the flange closing the end of the tubular chamber. It is locked in place by a screw on the underside of the cover Sheet 8—

Sheet 9—

Shows the views of the different positions of the jaws in one cycle of operation:

Sheet 10—

Demonstrates the different positions of the jaws and the instrument in the tying process:

Sheet 12—

Sheet 13—

DETAILED DESCRIPTION OF THE PREFERRED EMBODIMENT

The grasper sub-assemblies are first assembled. The upper and lower jaws, are combined with their rods and their sheaths to form the right (1) and left (2) grasper sub-assemblies. The front-spacer is then mounted on to them, followed by the main sheath from the rear to the front. The rear-spacer is then mounted from the rear, completing the "main sub assembly". Adhesives are applied. Note, the main sheath is trapped between the shoulders on the two spacers. Sheath-1 is then locked down with the mini-screw onto the rear spacer, so it becomes stationary. The following are then mounted onto Rod-1: Adaptor-5, Adaptor-4, the Spring-1, the Washer and the Ball. The following are then mounted onto Rod-2: Adaptor-3, U-shaped Adaptor 4A, Free-Wheeling Adaptor 4B, the Spring-2, then Mini-Adaptor 5A, Free-Wheeling Adaptor 5B, and the Rod-Extension. It is extremely important that when the adaptors are locked down with mini-screws, they must be first placed in the correct orientation, to avoid mutual interference.

The completed "main sub-assembly" is then gently inserted into the rear end of the chamber located on the top of the Sationary handle and is locked down with mini-screws. The movable handle is brought into the recess on its upper end and makes a joint with the ball, and mounted with the hinge screws. The rear plug (different from the rear spacer) is mounted last and is locked down with a screw on the underside of its flange. The 4 levers are attached to their respective adaptors in the slots.

The invention claimed is:

1. A laparoscopic surgical instrument capable of tying a knot in a free strand of suture intra-abdominally comprising:
    two small diameter laparoscopic graspers each having shafts housed within a common external sheath, each grasper having an operating mechanism housed within a common tubular chamber at the top of a stationary member of a scissors type of handle assembly having a movable handle, with only one of the grasper; operated by the movable handle, and acting as a recipient grasper; and a second grasper of the graspers not connected to the handle but is rotatable, and slide-able, and acting as a donor grasper;
    a narrow gap between tips of the graspers for trapping a tail strand of the suture;
    a first lever inside an angled slot on a front side-wall of the tubular chamber, capable of automatically generating rotation or de-rotation of the donor grasper during an angled forward or backward sliding within the slot;
    a second lever inside a separate long horizontal slot on the same side wall of the tubular chamber, with a free-wheel connection to a shaft of the donor grasper, capable of producing simple forward or backward sliding of the donor grasper, whilst also simultaneously producing passive rotation or de-rotation of the donor grasper, on account of the movement of the first lever within the angled slot, without having the second lever itself rotating;
a third lever at the rear of the long horizontal slot, with a freewheel connection to the shaft of the donor grasper, wherein forward-sliding of the third lever results in opening of jaws of the donor grasper, irrespective of any simultaneous rotation;
a compression spring, said compression spring biasing an upper jaw of the donor grasper towards a closed position;
a second compression spring biasing jaws of the recipient grasper towards an open position.

2. A method of tying a knot in a free length of suture laparoscopically and intra-abdominally comprising:
providing the laparoscopic instrument of claim 1;
providing a suture having a head end and a tail end;
passing the head end of the suture from the jaws of the donor grasper, behind the tail strand of the suture, to the jaws of the recipient grasper, thus forming a knot; the method further comprising:
first steadying the tail end of the suture with a separate laparoscopic grasper in a surgeon's non-dominant hand, followed by, using the instrument of claim 1 in the surgeon's dominant hand to enter an abdominal cavity from a side opposite to the surgeon;
crossing the instrument of claim 1 over and above the tail end; pushing forwards the donor grasper while simultaneously rotating it 90 degrees to the left and causing jaws of the donor grasper to lie in a vertical plane;
grasping the head end of the suture with the jaws of the donor grasper in a protruded position;
pulling back the entire instrument of claim 1 over the tail end, carrying the head end of the suture in the protruded jaws, and then advancing the entire instrument of claim 1 forwards again, thereby trapping the tail end in the gap between the tips of the two graspers, with the tip of the donor grasper under the tail strand;
pulling back the donor grasper, automatically de-rotating its jaws 90 degrees, thereby returning to an original position and orientation, and placing the head end of the grasped suture automatically within jaws of the recipient grasper;
finally closing the jaws of the recipient grasper, thereby taking over the head end of the suture, and pulling it away forming the knot.

\* \* \* \* \*